US007270820B2

(12) United States Patent
Diepolder et al.

(10) Patent No.: US 7,270,820 B2
(45) Date of Patent: *Sep. 18, 2007

(54) CD4+ T-LYMPHOCYTE-SPECIFIC HEPATITIS C VIRUS EPITOPES

(75) Inventors: Helmut Diepolder, München (DE); Maria-Christina Jung, München (DE)

(73) Assignee: Immusystems GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/962,145

(22) Filed: Oct. 7, 2004

(65) Prior Publication Data

US 2005/0249754 A1 Nov. 10, 2005

Related U.S. Application Data

(63) Continuation of application No. PCT/EP03/03732, filed on Apr. 10, 2003.

(30) Foreign Application Priority Data

Apr. 10, 2002 (EP) .................................. 02008033

(51) Int. Cl.
*A61K 39/00* (2006.01)
*A61K 39/12* (2006.01)
*A61K 39/29* (2006.01)
*C07K 7/00* (2006.01)

(52) U.S. Cl. ................. 424/189.1; 424/184.1; 424/185.1; 424/186.1; 424/228.1; 424/278.1; 530/300; 514/2

(58) Field of Classification Search ............. 424/184.1, 424/185.1, 186.1, 189.1, 204.1, 225.1, 228.1; 435/4, 5, 7.1; 514/2; 530/300, 326, 327, 530/328, 350
See application file for complete search history.

(56) References Cited

U.S. PATENT DOCUMENTS

| 5,980,899 | A | * | 11/1999 | Berzofsky et al. | ....... | 424/185.1 |
| 6,007,982 | A | | 12/1999 | Deleys et al. | | |
| 6,027,729 | A | * | 2/2000 | Houghton et al. | ....... | 424/228.1 |
| 6,183,949 | B1 | | 2/2001 | Seidel et al. | | |
| 6,221,355 | B1 | * | 4/2001 | Dowdy | .................... | 424/192.1 |
| 6,689,363 | B1 | * | 2/2004 | Sette et al. | ............. | 424/189.1 |
| 2003/0186224 | A1 | * | 10/2003 | Gerlach et al. | ................ | 435/5 |

FOREIGN PATENT DOCUMENTS

| EP | 0 501 557 A1 | | 9/1992 |
| EP | 0 518 313 A | | 12/1992 |
| EP | WO 01/68820 | * | 9/2001 |
| WO | WO 01/21189 A1 | | 3/2001 |
| WO | WO 01/90197 A1 | | 11/2001 |
| WO | WO 02/04484 A2 | | 1/2002 |
| WO | WO 02/26785 A2 | | 4/2002 |

OTHER PUBLICATIONS

Bowie et al., Deciphering the Message in Protein Sequences: Tolerance to Amino Acid Substitutions, Science, vol. 247 No. 4948, pp. 1306-1310 (Mar. 1990).*
Diepolder et al., The role of hepatitis C virus specific CD4+ T lymphocytes in acute and chronic hepatitis, Journal of Molecular Medicine, vol. 74 No. 10, pp. 583-588 (Oct. 1996).*
Lauer et al., Comprehensive Analysis of CD8+-T-Cell Responses against Hepatitis C Virus Reveals Multiple Unpredicted Specificities, Journal of Virology, vol. 76 No. 12, pp. 6104-6113 (Jun. 2002).*
LeRoux-Roels, Development of prophylactic and therapeutic vaccines against hepatitis C virus, Expert Review of Vaccines, vol. 4 No. 3, pp. 351-371 (Jun. 2005).*
Schulze zur Wiesch et al., Broad Repertoire of the CD4+ Th Cell Response in Spontaneously Controlled Hepatitis C Virus Infection Includes Dominant and Highly Promiscuous Epitopes, Journal of Immunology, vol. 175 No. 6, pp. 36.3-3613 (Sep. 2005).*
Shirai et al., Induction of cytotoxic T cells to a cross-reactive epitope in the hepatitis C virus nonstructural RNA polymerase-like protein, Journal of Virology, vol. 66 No. 7, pp. 4098-4106 (Jul. 1992).*
Schirren et al., Antiviral treatment of recurrent hepatitis C virus (HCV) infection after liver transplantation . . . , Journal of Hepatology, vol. 39 No. 3, pp. 397-404 (Sep. 2003).*
Uno-Furuta et al., Induction of virus-specific cytotoxic T lymphocytes by in vivo electric administration of peptides, Vaccine, vol. 19 Nos. 15-16, pp. 2190-2196 (Feb 2001).*
Takamizawa et al., "Structure and organization of the hepatitis C virus genome isolated from human carriers," Journal of Virology, vol. 65 No. 3, pp. 1105-1113 (Mar. 1991).*
Trowbidge, R. et al., "*Molecular clonging of an Australian isolate of hepatitis C virus*", Arch. Virol, vol. 143(3), (1998), pp. 501-511, no date available.
Takamizawa, A et al., "*Structure and organization of the hepatitis C virus genome isolated from human carriers*", J. Virol, vol. 65(3), (1991), pp. 1105-1113, no date available.
Yanagi, M., et al., "*Transcripts from a single full-length cDNA clone of hepatitis C virus are infectious when directly transfected into the liver of chimpanzee*", Proc. Natl. Acad. Sci. U.S.A. vol. 94(16), (1997), pp. 8738-8743, no date available.
Okamoto, H., et al., "*Nucleotide sequence of the genomic RNA of hepatitis C virus isolated from a human*", J. Gen. Virol., vol. 72(Pt 11), (1991), pp. 2697-2704, no date available.
Okamoto, H., et al., "*Full-length sequence of a hepatitis C virus genome having poor homology to reported isolates: comparative study of four distinct genotypes*", Virology, vol. 188(1), (1992), pp. 331-341, no date available.
Choo, Q.L., et al., "*Genetic organization and diversity of the hepatitis C virus*", Proc. Natl. Acad. Sci. U.S.A., vol. 88(6), (1991), pp. 2451-2455, no date available.
Tanaka, T., et al., "*Molecular cloning of hepatitis C virus genome from a single Japanese carrier: sequence variation within the same individual and among infected individuals*", Virus Res. vol. 23(1-2), (1992), pp. 39-53, no date available.

(Continued)

Primary Examiner—Bruce Campell
Assistant Examiner—Zachariah Lucas
(74) *Attorney, Agent, or Firm*—Foley & Lardner LLP

(57) ABSTRACT

The invention relates to hepatitis C virus epitopes which are CD4+ T-lymphocyte specific, and to vaccines containing these epitopes.

3 Claims, No Drawings

OTHER PUBLICATIONS

Kato, N., et al., "*Molecular cloning of the human hepatitis C virus genome from Japanese patients with non-A, non-B hepatitis*", Proc. Natl. Acad. Sci. U.S.A. vol 87(24), (1990), pp. 9524-9528, no date available.

Chen, P.J., et al., "*The Taiwanese hepatitis C virus genome": sequence determination and mapping the 5'termini of viral genomic and antigenomic RNA*, Virology, vol. 188(1), (1992), pp. 102-113, no date available.

Inchauspe, G., et al., "*Genomic structure of the human prototype strain H of hepatitis C virus: comparison with American and Japanese isolates*", Proc. Natl. Acad. Sci. U.S.A., vol. 88(22) (1991), pp. 10292-10296, no date available.

Chayama, K., "*Toranomon Hospital, Department of Gastroenterology*"; 2-2-2 Toranomon, Minato-ku, Tokyo 105, Japan: "Direct Submission", Submitted (Feb. 18, 1995) to the DDBJ/EMBL/GenBank databases; Comment: D26556: Submitted (Jan. 20, 1994) to DDBJ by: Kazuaki Chayama.

Chamberlain, R.W., et al., "*Complete nucleotide sequence of a type 4 hepatitis C virus variant, the predominant genotype in the Middle East*", J. Gen Virol., vol. 78(Pt 6), (1997), pp. 1341-1347, no date available.

Chamberlain, R.W., et al., "*The complete coding sequence of hepatitis C virus genotype 5a, the predominant genotype in South Africa*", Biochem. Biophys. Res. Commun., vol. 236(1), (Jul. 1997), pp. 44-49.

Adams, N.J., et al., "*Complete coding sequence of hepatitis C virus genotype 6a*", Biochem. Biophys. Res. Commun., vol. 234(2), (1997), pp. 393-396, no date available.

Honda, M., et al., "*Sequence comparisons for a hepatitis C virus genome RNA isolated from a patient with liver cirrhosis*", Gene, vol. 120(2), (1992), pp. 317-318, no date available.

Okamoto, H., et al., "*Genetic drift of hepatitis C virus during an 8.2-year infection in a chimpanzee: variability and stability*", Virology, vol. 190(2), (1992), pp. 894-899, no date available.

Choo, Q.L., et al., "*Isolation of a cDNA clone derived from a blood-borne non-A, non-B viral hepatitis genome*", Science, vol. 244(4902), (Apr. 21, 1989), pp. 359-362.

"*Primary consensus sequence complete 1b genomes available in EMBL database*", (Jan. 2000).

Diepolder, et al., "*Immunodominant CD4+ T-Cell Epitope within Nonstructural Protein 3 in Acute Hepatitis C Virus Infection*", Journal of Virology, (Aug. 1997), pp. 6011-6019.

Khudyakov, Yu. E., et al., "*Linear B-cell epitopes of the NS3-NS4-NS5 proteins of the hepatitis C virus as modelled with synthetic peptides*", Virology, vol. 206(1), (1995), pp. 666-672, no date available.

Qi Z, et al., "*Clone Q379 immunoscreened from a Chinese HCV cDNA lambda gt11 library*", Current Microbiology, United States, Bd. 28, No. 3, (Mar. 1994), pp. 161-163.

Ramsay, A.J., et al., "*DNA vaccination against virus infection and enhancement of antiviral immunity following consecutive immunization with DNA and viral vectors*", Immunology and Cell Biology, vol. 75, (1997), pp. 382-388, no date available.

Database TREMBL 'online!; Polyprotein (Fragment) from *Hepatitis C virus*, (Nov. 1, 1996), retrieved from EBI; Database accession No. q68529; XP002208337, abstract, no date available.

* cited by examiner

SEQUENCE LISTING

<160> NUMBER OF SEQ ID NOS: 17

<210> SEQ ID NO 1
<211> LENGTH: 15
<212> TYPE: PRT
<213> ORGANISM: Hepatitis C virus

<400> SEQUENCE: 1

Gly Pro Arg Leu Gly Val Arg Ala Thr Arg Lys Thr Ser Glu Arg
1               5                   10                  15

```
<210> SEQ ID NO 2
<211> LENGTH: 15
<212> TYPE: PRT
<213> ORGANISM: Hepatitis C virus

<400> SEQUENCE: 2

Ala Arg Ser Leu Thr Pro Cys Thr Cys Gly Ser Ser Asp Leu Tyr
 1               5                  10                  15

<210> SEQ ID NO 3
<211> LENGTH: 15
<212> TYPE: PRT
<213> ORGANISM: Hepatitis C virus

<400> SEQUENCE: 3

Ser Ser Asp Leu Tyr Leu Val Thr Arg His Ala Asp Val Ile Pro
 1               5                  10                  15

<210> SEQ ID NO 4
<211> LENGTH: 15
<212> TYPE: PRT
<213> ORGANISM: Hepatitis C virus

<400> SEQUENCE: 4

Met Trp Lys Cys Leu Ile Arg Leu Lys Pro Thr Leu His Gly Pro
 1               5                  10                  15

<210> SEQ ID NO 5
<211> LENGTH: 15
<212> TYPE: PRT
<213> ORGANISM: Hepatitis C virus

<400> SEQUENCE: 5

Val Leu Val Asp Ile Leu Ala Gly Tyr Gly Ala Gly Val Ala Gly
 1               5                  10                  15

<210> SEQ ID NO 6
<211> LENGTH: 20
<212> TYPE: PRT
<213> ORGANISM: Hepatitis C virus

<400> SEQUENCE: 6

Thr His Tyr Val Pro Glu Ser Asp Ala Ala Ala Arg Val Thr Gln Ile
 1               5                  10                  15

Leu Ser Ser Leu
            20

<210> SEQ ID NO 7
<211> LENGTH: 20
<212> TYPE: PRT
<213> ORGANISM: Hepatitis C virus

<400> SEQUENCE: 7

Thr Ile Thr Gln Leu Leu Lys Arg Leu His Gln Trp Ile Asn Glu Asp
 1               5                  10                  15

Cys Ser Thr Pro
            20

<210> SEQ ID NO 8
<211> LENGTH: 20
<212> TYPE: PRT
<213> ORGANISM: Hepatitis C virus
```

-continued

```
<400> SEQUENCE: 8

Cys Ser Gly Ser Trp Leu Arg Asp Val Trp Asp Trp Ile Cys Thr Val
 1               5                  10                  15

Leu Thr Asp Phe
            20

<210> SEQ ID NO 9
<211> LENGTH: 20
<212> TYPE: PRT
<213> ORGANISM: Hepatitis C virus

<400> SEQUENCE: 9

Gly Ala Gln Ile Thr Gly His Val Lys Asn Gly Ser Met Arg Ile Val
 1               5                  10                  15

Gly Pro Lys Thr
            20

<210> SEQ ID NO 10
<211> LENGTH: 20
<212> TYPE: PRT
<213> ORGANISM: Hepatitis C virus

<400> SEQUENCE: 10

Glu Val Thr Arg Val Gly Asp Phe His Tyr Val Thr Gly Met Thr Thr
 1               5                  10                  15

Asp Asn Val Lys
            20

<210> SEQ ID NO 11
<211> LENGTH: 20
<212> TYPE: PRT
<213> ORGANISM: Hepatitis C virus

<400> SEQUENCE: 11

Cys Pro Cys Gln Val Pro Ala Pro Glu Phe Phe Thr Glu Val Asp Gly
 1               5                  10                  15

Val Arg Leu His
            20

<210> SEQ ID NO 12
<211> LENGTH: 20
<212> TYPE: PRT
<213> ORGANISM: Hepatitis C virus

<400> SEQUENCE: 12

Phe Thr Glu Val Asp Gly Val Arg Leu His Arg Tyr Ala Pro Ala Cys
 1               5                  10                  15

Lys Pro Leu Leu
            20

<210> SEQ ID NO 13
<211> LENGTH: 20
<212> TYPE: PRT
<213> ORGANISM: Hepatitis C virus

<400> SEQUENCE: 13

Thr Ser Met Leu Thr Asp Pro Ser His Ile Thr Ala Glu Thr Ala Lys
 1               5                  10                  15

Arg Arg Leu Ala
            20
```

-continued

```
<210> SEQ ID NO 14
<211> LENGTH: 20
<212> TYPE: PRT
<213> ORGANISM: Hepatitis C virus

<400> SEQUENCE: 14

Ser Ser Ser Ala Ser Gln Leu Ser Ala Pro Ser Leu Lys Ala Thr Cys
  1             5                   10                  15

Thr Thr His His
             20

<210> SEQ ID NO 15
<211> LENGTH: 20
<212> TYPE: PRT
<213> ORGANISM: Hepatitis C virus

<400> SEQUENCE: 15

Arg Glu Val Ser Val Ala Ala Glu Ile Leu Arg Lys Ser Arg Lys Phe
  1             5                   10                  15

Pro Pro Ala Met
             20

<210> SEQ ID NO 16
<211> LENGTH: 20
<212> TYPE: PRT
<213> ORGANISM: Hepatitis C virus

<400> SEQUENCE: 16

Pro Leu Leu Glu Ser Trp Lys Asp Pro Asp Tyr Val Pro Pro Val Val
  1             5                   10                  15

His Gly Cys Pro
             20

<210> SEQ ID NO 17
<211> LENGTH: 20
<212> TYPE: PRT
<213> ORGANISM: Hepatitis C virus

<400> SEQUENCE: 17

Asp Val Val Cys Cys Ser Met Ser Tyr Thr Trp Thr Gly Ala Leu Ile
  1             5                   10                  15

Thr Pro Cys Ala
             20
```

CD4+ T-LYMPHOCYTE-SPECIFIC HEPATITIS C VIRUS EPITOPES

CROSS-REFERENCE TO RELATED APPLICATIONS

This application is a continuation of International Patent Application No. PCT/EP03/03732, filed Apr. 10, 2003, which claims priority to European Patent Application No. 02008033.9, filed Apr. 10, 2002, each of which is hereby incorporated by reference in its entirety.

The invention relates to hepatitis C virus epitopes which are CD4+ T-lymphocyte specific, and to vaccines that contain these epitopes.

The hepatitis C virus, called HCV in the following, was identified in 1989 and is an RNA virus from the family of Flaviviridae. It consists of a single RNA strand of approx. 9400 nucleotides which encode a precursor polyprotein approx. 3,000 amino acids long. This polyprotein is translated in an open reading frame and split proteolytically after translation. The virus is highly variable, and various virus isolates exist which are designated as genotypes and whose geographical distribution varies considerably. A distinction is made between more than six genotypes worldwide today. These genotypes are subdivided in turn into sub-types. The genetic variability exists inter-individually and intra-individually (within an infected individual). The intra-individual subtypes are the so-called HCV quasispecies, which are related but different virus sequences which form where there is imprecise replication.

With a prevalence of approx. one to three percent worldwide, hepatitis C is one of the most significant chronic virus infections. At present, it is assumed that at least 180 million people are infected. According to calculations by the Centers for Disease Control in the USA, because of the long latency period after infection with the HCV, there will, in addition, be a rise in diseases associated with hepatitis C by the year 2010.

The HCV is mainly transmitted parenterally and was, until its discovery, the main cause of non-A, non-B post-transfusion hepatitis. The routine testing of all blood products with 2nd and 3rd generation HCV-antibody tests has dramatically reduced the number of post-transfusion hepatitides. "Sporadic" hepatitis C and i.v. drug abuse are now regarded as the main routes for the transmission of new HCV infections. At the moment, there are no known measures for effectively preventing new infections caused in these ways.

The HCV causes chronic liver inflammation (hepatitis) which, over the course of many years, can lead to further complications such as cirrhosis of the liver. Where cirrhosis of the liver exists for years, around 5% of all infected persons will develop a hepatocellular carcinoma. In the Western world, hepatitis C is therefore the primary indication of the need for a liver transplant. The costs of these transplants for the health service are considerable.

With chronic hepatitis C, antibodies have been detected against almost all virus proteins, but, in contrast to hepatitis B, there is no anti-HCV antibody constellation which displays an immunity to HCV or any healing capacity. Nor does the presence of antibodies against the HCV during a chronic HCV infection reduce its progression. On the contrary, successful treatment seems to be associated with a lowering of the antibody titre. It is therefore not possible to prevent an infection with hepatitis C through the use of a conventional prophylactic inoculation with envelope protein, as has been done successfully with hepatitis B. No prophylactic inoculation is therefore available at the moment.

The only currently approved therapy for chronic hepatitis C is a treatment with Interferon alpha alone or in combination with Ribavirin for 6 to 12 months. This form of therapy is very cost-intensive, has considerable side-effects and only leads to a permanent elimination of the virus in approx. 50% of cases. Peptide epitopes containing T-cell epitopes have already been identified (Diepolder et al., J. Virol. 1997; EP: 00 121 138.2; PCT: WO 02/26785A2). These epitopes were identified in a patient collective through the culture of virus-specific CD4+ T-cell clones.

In addition, systematic investigations to date have essentially been based on data obtained from patients with a chronic hepatitis C infection, and a spontaneous elimination of the virus at the point in time when a chronic HCV infection already exists is extremely rare. Epitopes which were found in patients with a chronic HCV infection are therefore not associated with the healing of the disease.

For this reason, the object of the present invention is the identification of HCV epitopes which are CD4+ T-lymphocyte specific and which are associated with virus elimination or virus suppression.

This object is solved by CD4+ T-lymphocyte-specific HCV epitopes with an impact factor (IF)$\geq$mean value (MV)+2*Sta, where $$IF = \frac{n_1 * 1 + n_2 * 1.5}{m} * 100 \qquad \text{(formula 1)}$$

where
  $n_1$ is the sum of the reactions with 3<SI<6,
  $n_2$ is the sum of the reactions with SI$\geq$6 and
  m is the number of tests against the peptide in question, whereby m$\geq$15 and MV is the mean value of all impact factors.

Preference is given to the impact factor of the CD4+ T-lymphocyte-specific HCV epitopes>MV and $\leq$MV+1*Sta, especially >MV+1*Sta and <MV+2*Sta, with particular preference for $\geq$MV+2*Sta.

A preferred solution to the task is CD4+ T-lymphocyte-specific HCV epitopes, covering one or more peptides, selected from the group (SEQ ID NOS: 1-17):
(EP001) GPRLGVRATRKTSER,
(EP002) ARSLTPCTCGSSDLY,
(EP003) SSDLYLVTRHADVIP,
(EP004) MWKCLIRLKPTLHGP,
(EP005) VLVDILAGYGAGVAG,
(EP006) THYVPESDAAARVTQILSSL,
(EP007) TITQLLKRLHQWINEDCSTP,
(EP008) CSGSWLRDVWDWICTVLTDF,
(EP009) GAQITGHVKNGSMRIVGPKT,
(EP010) EVTRVGDFHYVTGMTTDNVK,
(EP011) CPCQVPAPEFFTEVDGVRLH,
(EP012) FTEVDGVRLHRYAPACKPLL,
(EP013) TSMLTDPSHITAETAKRRLA,
(EP014) SSSASQLSAPSLKATCTTHH,
(EP015) REVSVAAEILRKSRKFPPAM,
(EP016) PLLESWKDPDYVPPVVHGCP, and
(EP017) DVVCCSMSYTWTGALITPCA and derivatives hereof with the same or similar specificity.

A further preferred solution to the task are the CD4+ T-lymphocyte-specific HCV epitopes listed below, containing the sequence (SEQ ID NOS: 1-17):
EP001 GPRLGVRATRKTSER
EP002 ARSLTPCTCGSSDLY
EP003 SSDLYLVTRHADVIP
EP004 MWKCLIRLKPTLHGP
EP005 VLVDILAGYGAGVAG
EP006 THYVPESDAAARVTQILSSL
EP007 TITQLLKRLHQWINEDCSTP
EP008 CSGSWLRDVWDWICTVLTDF
EP009 GAQITGHVKNGSMRIVGPKT
EP010 EVTRVGDFHYVTGMTTDNVK
EP011 CPCQVPAPEFFTEVDGVRLH
EP012 FTEVDGVRLHRYAPACKPLL
EP013 TSMLTDPSHITAETAKRRLA
EP014 SSSASQLSAPSLKATCTTHH
EP015 REVSVAAEILRKSRKFPPAM
EP016 PLLESWKDPDYVPPVVHGCP and/or
EP017 DVVCCSMSYTWTGALITPCA.

Particular preference is given to the CD4+ T-lymphocyte-specific HCV epitopes according to the invention, selected from the group of epitopes EP001 to EP017 with the above-named sequence. These epitopes EP001 to EP017 according to the invention have an impact factor of $\geq$MV+2*Sta.

Because these epitopes are to be used further for an immune therapy of chronic hepatitis C or a vaccine, further criteria are a high degree of conservation between various virus sub-types and a high degree of promiscuity of binding to various HLA class II molecules. The HCV epitopes identified and characterised in this way are to be available for a vaccine for the prevention and/or treatment of an HCV infection.

To solve the task, a unique patient collective was identified, namely patients with acute hepatitis C who reach a lasting or at least temporary virus elimination in over 50% of cases. In order to test all possible CD4+ T-cell epitopes, the whole virus was covered with overlapping synthetic peptides from 15 to 20 amino acids long. A standardised lymphocyte proliferation assay was used as the test system. In order to determine both the degree of conservation between various virus sub-types and also the binding promiscuity as regards the relevant genetic background of the patients, a formula was defined based on the frequency of detection of an epitope and the strength of the immune reaction in question.

The invention is based on the selection of a special patient collective, studies with defined peptides and an algorithm to identify highly immunogenic CD4+ T-cell epitopes which are suitable for the development of a prophylactic or therapeutic vaccine.

The algorithm determines the "impact factor" (IF) of the epitope in question and is defined as follows:

$$IF = \frac{n_1 * 1 + n_2 * 1.5}{m} * 100 \quad \text{(formula 1)}$$

where
$n_1$ is the sum of the reactions with 3<SI<6,
$n_2$ is the sum of the reactions with SI$\geq$6 and
m is the number of tests carried out against the peptide in question; this is used for standardisation of the values.
In the case of the peptides found by us, m was $\geq$15.

The stimulation index (SI) is normally calculated from the raw data of a proliferation assay and represents the multiplication factor of the measured sample in comparison with the control. An SI of 3 is regarded as significant.

In addition, the mean value was calculated from the impact factor of all the tested peptides, whereby every impact factor was determined according to formula 1. In order to determine relevant epitopes with statistical precision, our solution to the task is limited to the peptides whose IFs are two standard deviations above the mean value of all IFs.

Under the terms of the present invention, "CD4+ T-lymphocyte-specific HCV epitopes" means a defined region of a hepatitis C protein which, because of its structure, "fits" into the complementary binding site of a CD4+ T-lymphocyte receptor and thus triggers a reaction highly specifically.

Because the primary amino acid structure of the HCV proteins is known, over 450 synthetic peptides (15-20-mers) were used here in total, which each overlap between 5 and 10 amino acids and cover the known structured and non-structured proteins.

Collective:

A special patient collective was chosen and examined for HCV specific CD4+ T-cell epitopes relevant for the healing of the disease. The patient collective, namely patients with acute hepatitis C, is difficult to identify, since, on the one hand, they occur with a frequency of approx. 1:100,000 in the German population and, on the other hand, only T-lymphocytes were tested in the acute phase of the disease. This means a considerable limitation in the number of usable samples. Finally, within this patient collective, only patients were considered who were able to clear the virus spontaneously or to control it temporarily (this is only approx. 60% of the patients with acute hepatitis C), since only here has the immune system successfully taken action against the virus.

In contrast, a spontaneous elimination of the virus at a later time (chronic HCV) is a rarity. In the late, chronic phase, there is also only a small or undetectable CD4+ T-cell response against the virus. Epitopes which are associated with temporary or permanent virus control in particular are therefore of outstanding importance. These epitopes or the measured reaction to these peptides are therefore associated directly or indirectly with the healing of the HCV infection and are thus ideal candidates for future "peptide inoculations". This is the case with the peptide sequences or peptides according to the invention.

Peptides:

A "peptide screening" with approx. 450 selected different peptides (15-22-mers) was carried out as regards a virus-specific CD4+ T-cell response with the patient collective described above.

The peptides represent the entire virus protein, whereby we used 15-mers with 5 amino acid long overlapping areas and 20-22-mers with 10 amino acid overlapping areas in order to cover all possible relevant epitopes.

Table 1 shows the various positions in the HCV genome of the epitopes according to the invention, giving the relevant virus isolate reference (Table 1, column 4). The information on the amino acid position (Table 1, column 2) are only to be understood as approximations, since, because of the high mutation rate of the virus with the various virus isolates, there may be changes in position. The conserved epitopes should probably be seen as particularly important for prophylactic and therapeutic inoculations, as reflected in the consistent sequence of the different virus isolates of an epitope (see also Table 1, column 5).

Earlier investigations of our own had shown that particular areas of the virus have a special immunological significance, and so these areas of the virus genome (NS3-NS4) were additionally tested using peptides (20-mers with 10 amino acid long overlapping areas).

Table 1 (SEQ ID NOS: 1-17, respectively, in order of appearance):

TABLE 1

| No. | Item | IF | Amino acid sequence | Virus isolate reference (see list 1) |
|---|---|---|---|---|
| EP001 | 40 | 24.0 | GPRLGVRATRKTSER | c, 3, 4, 5, 6, 8, 10, 12, 14, 15, 16 |
| EP002 | 1120 | 27.6 | ARSLTPCTCGSSDLY | c, 1, 2, 7, 9 |
| EP003 | 1130 | 23.2 | SSDLYLVTRHADVIP | c, 1, 2, 3, 6, 7, 9, 10, 15, 16 |
| EP004 | 1610 | 24.1 | MWKCLIRLKPTLHGP | c, 1, 2, 3, 6, 7, 8, 12, 15, 16 |
| EP005 | 1850 | 24.1 | VLVDILAGYGAGVAG | c, 1, 2, 7, 8, 10, 15, 16 |
| EP006 | 1935 | 26.7 | THYVPESDAAARVTQILSSL | c, 1, 2, 7, 8, 16 |
| EP007 | 1955 | 43.8 | TITQLLKRLHQWINEDCSTP | c, 1, 2, 7, 8, 16 |
| EP008 | 1975 | 23.3 | CSGSWLRDVWDWICTVLTDF | c, 1, 2, 15, 16 |
| EP009 | 2035 | 23.3 | GAQITGHVKNGSMRIVGPKT | c, 1, 2, 7, 8, 15 |
| EP010 | 2095 | 21.9 | EVTRVGDFHYVTGMTTDNVK | c, 1, 2, 8, 15, 16 |
| EP011 | 2115 | 23.3 | CPCQVPAPEFFTEVDGVRLH | c, 1, 8, 9, 15, 16 |
| EP012 | 2125 | 28.1 | FTEVDGVRLHRYAPACKPLL | c, 1, 9, 15, 16 |
| EP013 | 2175 | 26.7 | TSMLTDPSHITAETAKRRLA | c, 2, 7, 8, 9, 15, 16 |
| EP014 | 2205 | 23.3 | SSSASQLSAPSLKATCTTHH | c, 2, 7, 8, 16 |
| EP015 | 2275 | 25.0 | REVSVAAEILRKSRKFPPAM | c |
| EP016 | 2305 | 26.7 | PLLESWKDPDYVPPVVHGCP | c, 1, 2, 15, 16 |
| EP017 | 2425 | 23.3 | DVVCCSMSYTWTGALITPCA | c, 1, 2, 8, 16 |

List 1: Virus Isolates

1
Genotype: 1b AUTHORS Trowbridge, R. and Gowans, E. J.
TITLE Molecular cloning of an Australian isolate of hepatitis C virus
JOURNAL Arch. Virol. 143 (3), 501-511 (1998)

2
Genotype: 1b AUTHORS Takamizawa, A., Mori, C., Fuke, I., Manabe, S., Murakami, S., Fujita, J., Onishi, E., Andoh, T., Yoshida, I. and Okayama, H.
TITLE Structure and organization of the hepatitis C virus genome isolated from human carriers
JOURNAL J. Virol. 65 (3), 1105-1113 (1991)

3
Genotype: 1a AUTHORS Yanagi, M., Purcell, R. H., Emerson, S. U. and Bukh, J.
TITLE Transcripts from a single full-length cDNA clone of hepatitis C virus are infectious when directly transfected into the liver of a chimpanzee
JOURNAL Proc. Natl. Acad. Sci. U.S.A. 94 (16), 8738-8743 (1997)

4
Genotype: 2a AUTHORS Okamoto, H., Okada, S., Sugiyama, Y., Kurai, K., Ilzuka, H., Machida, A., Miyakawa, Y. and Mayumi, M.
TITLE Nucleotide sequence of the genomic RNA of hepatitis C virus isolated from a human
JOURNAL J. Gen. Virol. 72 (Pt 11), 2697-2704 (1991)

5
Genotype: 2b AUTHORS Okamoto, H., Kurai, K., Okada, S., Yamamoto, K., Lizuka, H., Tanaka, T., Fukuda, S., Tsuda, F. and Mishiro, S.
TITLE Full-length sequence of a hepatitis C virus genome having poor homology to reported isolates: comparative study of four distinct genotypes
JOURNAL Virology 188 (1), 331-341(1992)

6
Genotype: 1a AUTHORS Choo, Q.-L., Richman, K. H., Han, J. H., Berger, K., Lee, C., Dong C., Gallegos, C., Coit, D., Medina-Selby, A., Barr, P. J., Weiner, A. J., Bradley, D. W., Kuo, G. and Houghton, M.
TITLE Genetic organization and diversity of the hepatitis C virus
JOURNAL Proc. Natl. Acad. Sci. U.S.A. 88 (6), 2451-2455 (1991)

7
Genotype: 1b AUTHORS Tanaka, T., Kato, N., Nakagawa, M., Ootsuyama, Y., Cho, M. J., Nakazawa, T., Hijikata, M., Ishimura, Y. and Shimotohno, K.
TITLE Molecular cloning of hepatitis C virus genome from a single Japanese carrier: sequence variation within the same individual and among infected individuals
JOURNAL Virus Res. 23 (1-2), 39-53 (1992)

8
Genotype: 1b AUTHORS Kato, N., Hijikata, M., Ootsuyama, Y., Nakagawa, M., Ohkoshi, S., Sugimura, T. and Shimotohno, K.
TITLE Molecular cloning of the human hepatitis C virus genome from Japanese patients with non-A, non-B hepatitis
JOURNAL Proc. Natl. Acad. Sci. U.S.A. 87 (24), 9524-9528 (1990)

9
Genotype: 1b AUTHORS Chen, P. J., Lin, M. H., Tai, K. F., Liu, P. C., Lin, C. J. and Chen, D. S.
TITLE The Taiwanese hepatitis C virus genome: sequence determination and mapping the 5' termini of viral genomic and antigenomic RNA
JOURNAL Virology 188 (1), 102-113 (1992)

10
Genotype: 1a AUTHORS Inchauspe, G., Zebedee, S., Lee, D. H., Sugitani, M., Nasoff, M. and Prince, A. M.
TITLE Genomic structure of the human prototype strain H of hepatitis C virus: comparison with American and Japanese isolates
JOURNAL Proc. Natl. Acad. Sci. U.S.A. 88 (22), 10292-10296 (1991)

11
Genotype: 3b AUTHORS Chayama, K. Toranomon Hospital, Department of Gastroenterology; 2-2-2 Toranomon, Minato-ku, Tokyo 105, Japan TITLE Direct Submission
JOURNAL Submitted (18 Feb. 1995) to the DDBJ/EMBL/ GenBank databases
COMMENT D26556: Submitted (20 Jan. 1994) to DDBJ by: Kazuaki Chayama 12
Genotype: 4 AUTHORS Chamberlain, R. W., Adams, N., Saeed, A. A., Simmonds, P., Elliott, R. M.
TITLE Complete nucleotide sequence of a type 4 hepatitis C virus variant, the predominant genotype in the Middle East
JOURNAL J Gen Virol. June 1997; 78 (Pt 6):1341-7

13
Genotype: 5a AUTHORS Chamberlain, R. W., Adams, N. J., Taylor, L. A., Simmonds, P., Elliott, R. M.
TITLE The complete coding sequence of hepatitis C virus genotype 5a, the predominant genotype in South Africa
JOURNAL Biochem Biophys Res Commun. Jul. 9, 1997; 236 (1):44-9

14
Genotype: 6a AUTHORS Adams, N. J., Chamberlain, R. W., Taylor, L. A., Davidson, F., Lin, C. K., Elliott, R. M. and Simmonds, P.
TITLE Complete coding sequence of hepatitis C virus genotype 6a
JOURNAL Biochem. Biophys. Res. Commun. 234 (2), 393-396 (1997)

15
Genotype: 1b AUTHORS Honda, M., Kaneko, S., Unoura, M., Kobayashi, K. and Murakami, S.
TITLE Sequence comparisons for a hepatitis C virus genome RNA isolated from a patient with liver cirrhosis
JOURNAL Gene 120 (2), 317-318 (1992)

16
Genotype: 1b AUTHORS Okamoto, H., Kojima, M., Okada, S., Yoshizawa, H., Ilzuka, H., Tanaka, T., Muchmore, E. E., Peterson, D. A., Ito, Y. and Mishiro, S.
TITLE Genetic drift of hepatitis C virus during an 8.2-year infection in a chimpanzee: variability and stability
JOURNAL Virology 190 (2), 894-899 (1992)

17
Genotype: 1a AUTHORS Choo, Q. L., Kuo, G., Weiner, A. J., Overby, L. R., Bradley, D. W., Houghton, M.
TITLE Isolation of a cDNA clone derived from a blood-borne non-A, non-B viral hepatitis genome
JOURNAL Science Apr. 21, 1989 ; 244 (4902):359-82

C
Genotype: 1b
Primary consensus sequence complete 1b genomes available in EMBL database (January 2000)

Test System:
As the test system, the so-called "proliferation assay" was carried out according to the following protocol: After density gradient centrifugation on Ficoll gradients of heparinised blood, the fresh peripheral blood mononuclear cells (PBMC) were isolated and suspended in a culture medium (RPMI1640, Gibco). 50 µl of this cell suspension (concentration of $1\times10^6$ cells per ml) were placed on sterile 96-well culture plates. The cells were stimulated by the addition of the peptides. The final concentration of the peptides was 10 µg/ml. The cell culture plates were cultivated over 5 days at 37° C. and 5% $CO_2$, then mixed with $^3H$-thymidine and the incorporation of the radioactive $^3H$ was measured as a measure of the cell stimulation.

Evaluation:
In our studies, only peptide reactions were regarded as significant whose stimulation index (SI) was greater than 3 (3× higher compared with the controls, or the irrelevant peptides).

In order, on the one hand, to minimise the possibility of falsely positive reactions and irrelevant cross-reactions and, on the other hand, to create a hierarchy as regards the biological valency of relevant epitopes, an additional filter was defined and described in the following as the impact factor (IF).

The impact factor (IF) is based on a points system which not only uses the frequency of relevant reactions, i.e. stimulation index (SI) greater than 3, as normal, but also takes into account the strength of these reactions.

This assessment system was applied for every peptide tested and is defined according to the following formula:

$$IF = \frac{n_1 * 1 + n_2 * 1.5}{m} * 100 \qquad \text{(formula 1)}$$

where
$n_1$ is the sum of the reactions with 3<SI<6,
$n_2$ is the sum of the reactions with SI≧6 and
m is the number of tests against the peptide in question, whereby m≧15.

EXAMPLE

The following specific SIs (stimulation indexes) were measured against EP007 in 16 (m) independent tests: 0.91; 1.07; 1.10; 1.24; 1.32; 1.33; 1.40; 1.46; 1.81; 1.84; 3.01; 3.25; 4.38; 5.32; 7.58 and 12.77.

This produces $n_1$=4 (4 values>3 and <6); $n_2$=2 (2 values≧6), or, used in the formula $$IF = \frac{4+3}{16} * 100 \qquad \text{(formula 1)}$$

an impact factor of 43.75 for this peptide. Because, with the peptides tested by us, the mean value of all impact factors was 7.36 and the standard deviation was 6.75, this impact factor of 43.75 corresponds to a value of ≧MV+2*Sta. The relevant impact factor was calculated for every peptide tested. The mean value and standard deviation were then calculated from all the impact factors.

This then gives, depending on the level of the impact factor, a biologically and immunologically significant hierarchy. Peptides with a high impact factor are not only characterised by a high stimulation index, i.e. a strong specific reactivity, but also by the consistently specific reaction, i.e. found in different people.

The selection made here aims to give better consideration to the immunological valency of the peptides listed here. Epitopes which trigger HCV specific CD4+ T-cell responses which are strong and which are measured in different patients are of great relevance for future vaccine approaches.

The epitopes according to the invention are further characterised by the fact that a clear specific CD4+ T-cell activity to these peptides correlates with a reduction in the virus titre.

It is thus specifically these epitopes that would probably be ideal candidates for a vaccine. A specific inoculation reaction to these peptides could, on the one hand, prevent the disease and/or, on the other hand, lead to its cure, but could at least have a favourable influence on the course of an HCV infection.

The epitopes according to the invention are highly immunogenic, highly conserved HCV sequences which are partly positioned in the immediate vicinity of known CD8+ T-lymphocyte-specific HCV epitopes. As CD4+ T-lymphocyte-specific HCV epitopes, these can, in addition to the induction of CD4+ T-lymphocytes, also provide so-called T-cell assistance for cytotoxic CD8+ T-lymphocytes. These CD8+ T-lymphocytes are activated by the cytokines of stimulated CD4+ T-lymphocytes.

In addition, the peptides are characterised by frequent significant reaction in the case of various patients with different MHC (major histocompatibility complex) class II types. The MHC class II system is markedly polymorphic. The task of the MHC molecules is to bind peptide fragments originating from the body's own, pathogenic (e.g. hepatitis C virus) proteins and to express them for the detection and activation of specific CD4+ T-lymphocytes at the cell surface. This system facilitates an effective, specific immune response against pathogens such as HCV. Because various MHC class II types, i.e. different people, can express the same peptide on their MHC class II molecule, which is seen again in vitro in CD4+ activity that is directed against the same peptide and which can be measured in different people, it can be assumed that these peptides are promiscuous. This means that the epitopes according to the invention have an immunological relevance with various individuals.

In summary, specifically the epitopes according to the invention are extremely suitable both for a therapeutic and for a prophylactic peptide vaccine which is directed against the HCV.

A further solution is a vaccine which contains a combination of the epitopes EP001 to EP017 according to the invention. The vaccine may as a particular preference contain a mixture of the epitopes EP001 to EP017 according to the invention. However, further HCV epitopes may also be present.

The epitopes according to the invention may be used alone or with one or more auxiliary substances as a medication, preferably as a vaccine. The vaccine according to the invention contains at least one epitope according to the invention—preferably a mixture of epitopes according to the invention. However, further HCV epitopes may also be present.

The auxiliary substances are selected preferably from the group consisting of fowl pox virus, modified *vaccinia* virus Ankara, virosomes, TRANSVAX® (a tuberculosis epitope vaccine) and other substances reinforcing the immune reaction.

The vaccine according to the invention may be administered orally, parenterally, intramuscularly, intravenously, subcutaneously or intracutaneously.

The epitopes according to the invention are epitopes which can be used as T-cell-stimulating vaccine. A vaccine containing the epitopes according to the invention has the advantage over an inoculation with the entire virus protein, which contains the most different epitopes for virus-specific T-lymphocytes and only induces B-lymphocytes and CD4+ T-lymphocytes, that it selectively induces specific T-lymphocytes, CD4+ and/or CD8+ T-lymphocytes. In addition, it avoids antagonistic effects or the danger of iatrogenically produced autoimmune reactions which can appear following inoculation with whole proteins. The epitopes according to the invention have, in addition, a higher immunogenity in comparison with the entire virus protein, which means that a better vaccine result is achieved.

The vaccine according to the invention thus allows, in healthy people, the induction of an immune response and thus acts as a prophylactic vaccination. The vaccine according to the invention can also induce an immune response in chronically HCV-infected people and thus act as a therapeutic vaccine.

The encoding cDNA of these epitopes can be used in a DNA vaccine, a special method of vaccination. Here, the DNA encoding for the corresponding epitopes is cloned into a vector. This construct is then administered parenterally to the individual to be vaccinated (e.g. Immunology and Cell Biology, Volume 75, pages 382 to 388). According to the degenerated genetic code, various DNA sequences can encode one of the epitopes according to the invention (see Current protocols, Wiley).

The epitopes according to the invention can also be used in the diagnosis of the progress of an HCV infection, in that the volume of CD4+ T-lymphocytes which specifically recognise the epitope in question is monitored in the blood of the patient with a hepatitis C infection. This can be done, for example, with a diagnostic kit which comprises one or more of the epitopes according to the invention.

The disclosures of each and every patent, patent application, and publication cited herein are hereby incorporated herein by reference in their entirety.

What is claimed is:

1. A composition comprising at least one isolated $CD^{4+}$ T-lymphocyte-specific HCV epitope wherein the HCV epitope consists of (EP017) DVVCCSMSYTWTGALITPCA (SEQ ID NO: 17).

2. An immunogenic composition comprising the HCV epitope according to claim 1.

3. The immunogenic composition according to claim 2, additionally comprising at least one auxiliary substance selected from the group consisting of fowl pox virus, modified vaccinia virus Ankara, virosomes, CpG containing oligonucleotide, and other substances reinforcing the immune reaction.

* * * * *